(12) United States Patent
Dellimore et al.

(10) Patent No.: US 12,426,808 B2
(45) Date of Patent: Sep. 30, 2025

(54) SYSTEM AND METHOD FOR CORRECTING A SWEAT ANALYTE MEASUREMENT (71) Applicant: KONINKLIJKE PHILIPS N.V., Eindhoven (NL)

(72) Inventors: Kiran Hamilton J Dellimore, Eindhoven (NL); Mark Thomas Johnson, Eindhoven (NL); Ron Martinus Laurentius van Lieshout, Eindhoven (NL); Eduard Gerard Marie Pelssers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 939 days.

(21) Appl. No.: 17/617,024

(22) PCT Filed: Jun. 18, 2020

(86) PCT No.: PCT/EP2020/066846
§ 371 (c)(1),
(2) Date: Dec. 7, 2021

(87) PCT Pub. No.: WO2020/260107
PCT Pub. Date: Dec. 30, 2020

(65) Prior Publication Data
US 2022/0313123 A1     Oct. 6, 2022

(30) Foreign Application Priority Data

Jun. 26, 2019   (EP) ..................... 19182520

(51) Int. Cl.
*A61B 5/145*     (2006.01)
*A61B 5/00*      (2006.01)
*A61B 5/1486*    (2006.01)

(52) U.S. Cl.
CPC ........ *A61B 5/14517* (2013.01); *A61B 5/1486* (2013.01); *A61B 5/7278* (2013.01);
(Continued)

(58) Field of Classification Search
CPC . A61B 5/14517; A61B 5/1486; G01K 17/025
See application file for complete search history.

(56) References Cited

U.S. PATENT DOCUMENTS 4,266,556 A  *  5/1981  Barlow .................. G05D 23/20
                                                    219/442
5,131,390 A     7/1992  Sakaguchi
(Continued)

FOREIGN PATENT DOCUMENTS

CN      108414034 A    8/2018
EP       3242112 A1   11/2017

OTHER PUBLICATIONS

Hoppe, P. R. "Heat Balance Modeling" Institute and Outpatient Clinic for Occupational Medicine*, University of Munich, Ziemssenstr. 1, D-80336 München (Germany) (Year: 1993).*
(Continued)

*Primary Examiner* — Christian Jang (57) ABSTRACT

Provided is a system for correcting a sweat analyte measurement for temperature. The system comprises a sweat collector (106) for collecting sweat from skin (102). The collected sweat is drawn from the sweat collector to an outlet (110) via a capillary (108). The sweat is drawn through the capillary by capillary action and evaporation of the sweat from the outlet. The evaporation of the sweat from the outlet depends on the temperature. A flow sensor (112) measures a flow rate of the sweat being drawn through the capillary. An analyte sensor (114) obtains the sweat analyte measurement. The system further comprises a controller which is configured to determine a temperature from the measured flow rate. The sweat analyte measurement is then corrected using
(Continued)

the determined temperature. Further provided is a method for correcting a temperature-dependent sweat analyte measurement.

19 Claims, 4 Drawing Sheets

(52) U.S. Cl.
CPC ............... *A61B 2560/0252* (2013.01); *A61B 2560/0412* (2013.01)

(56) References Cited

U.S. PATENT DOCUMENTS

| | | | |
|---|---|---|---|
| 6,144,869 A * | 11/2000 | Berner | A61B 5/1486 600/347 |
| 2005/0069925 A1 | 3/2005 | Ford | |
| 2006/0004271 A1* | 1/2006 | Peyser | A61B 5/14532 600/362 |
| 2010/0009455 A1* | 1/2010 | Dosmann | G01N 27/3272 436/164 |
| 2010/0063372 A1* | 3/2010 | Potts | A61B 5/14521 600/346 |
| 2015/0087940 A1* | 3/2015 | Tatemoto | A61B 5/14546 600/345 |
| 2018/0263539 A1 | 9/2018 | Javey | |
| 2021/0204840 A1 | 7/2021 | Bertrand | |
| 2021/0311060 A1 | 10/2021 | Barnes | |

OTHER PUBLICATIONS

Nyein, Hnin Yin Yin et al., "A wearable microfluidic sensing patch for dynamic sweat secretion analysis", ACS sensors, vol. 3, No. 5, 2018, pp. 944-952.

Allan, J.R. et al., "Influence of acclimatization on sweat sodium concentration", Journal of Applied Physiology, vol. 30, No. 5, 1971, pp. 708-712.

Wilson, Thad E. et al., "Mean body temperature dose not modulate eccrine sweat rate during upright tilt", Journal of Applied Physiology. vol. 98, 2004, pp. 1207-1212.

Scharf, et al., "Regional differences in sweat rate response of steers to short-term heat stress", International Journal of Biometeorology, vol. 52, No. 8, 2008, pp. 725-732.

Ogai, K. et al., "Development of a small wireless device for perspiration monitoring", Medical Engineering & Physics, vol. 38, No. 4, 2016, pp. 391-397.

Mena-Bravo, A. et al., "Sweat: A sample with limited present applications and promising future in metabolomics", J. Pharm. Biomed. Anal. 90, 139-147 (2014).

Gao, W. et al. "Fully integrated wearable sensor arrays for multiplexed in situ perspiration analysis", Nature 529, 509-514 (2016).

International Search Report for PCT/EP2020/066846 filed Jun. 18, 2020.

Nie, C. et al: "A microfluidic device based on an evaporation-driven micropump", Biomedical Microdevices, Kluwer, Dordrecht, NL, vol. 17, No. 2, (Mar. 25, 2015), pp. 1-12.

Nie, C., "Integrated evaporation driven microfluidic device for continuous sweat monitoring". Eindhoven: University of Technology, Published May 4, 2016.

Anastasova, S. et al., "A wearable multisensing patch for continuous sweat monitoring". Biosensors and Bioelectronics 93 (2017) 139-145.

Lee, H. et al., "Wearable/disposable sweat-based glucose monitoring device with multistage transdermal drug delivery module". Sci. Adv. 2017;3:e1601314.

Nielsen, B. "Olympics in Atlanta: a fight against physics". Basic Sciences/Regulatory Physiology. Medicine and Science in Sports and Exercise, vol. 28, No. 6, Jun. 1996.

\* cited by examiner

SYSTEM AND METHOD FOR CORRECTING A SWEAT ANALYTE MEASUREMENT

CROSS-REFERENCE TO PRIOR APPLICATIONS

This application claims the priority benefit under 35 U.S.C. § 371 of International Patent Application No. PCT/EP2020/066846, filed on Jun. 18, 2020, which claims the priority benefit of European Patent Application No. 19182520.7, filed on Jun. 26, 2019, the contents of which are herein incorporated by reference.

FIELD OF THE INVENTION

This invention relates to a system and method for correcting a sweat analyte measurement according to the temperature.

BACKGROUND OF THE INVENTION

Non-invasive, semi-continuous and prolonged monitoring of biomarkers that indicate health and well-being is in demand for monitoring, for example, dehydration, stress, sleep, children's health and in perioperative monitoring.

Sweat, tear fluid and saliva may all be obtained non-invasively. Sweat is a particularly accessible biofluid, and is a rich source of information relating to the physiology and metabolism of the subject.

Some examples of clinical relevant components of sweat are $Na^+$, $Cl^-$ and/or $K^+$ to monitor dehydration, lactate as an early warning for inflammation (which is relevant to sepsis), glucose for diabetics and neonates, and cortisol in relation to sleep apnea and stress monitoring.

The development of reliable sweat sensing has, however, been hampered by several issues, in spite of clinical work showing promising results as early as the 1940s and 1950s. To date the impactful application of sweat analysis has been limited mainly to cystic fibrosis diagnostics, and drugs and alcohol abuse testing.

As summarized by Mena-Bravo and de Castro in "Sweat: A sample with limited present applications and promising future in metabolomics" J. Pharm. Biomed. Anal. 90, 139-147 (2014), it has been found that the results from sweat sensing can be highly variable, and a correlation between values determined from blood and sweat samples appears to be lacking for various biomarkers. However, historical studies in this area have involved relatively crude sampling techniques, such as collecting large sweat volumes in bags or textiles. Deficiencies in such techniques may have been a contributing factor to this apparent lack of correlation.

Access to sweat may be limited and uneven especially for individuals at rest in a non-thermal neutral state, having sweat rates as low as ~0.03-0.10 nl/min/gland. The term "non-thermal neutral state" means in this context that the individual is outside the thermal neutral zone in which the core body temperature remains very stable and there is no reason to induce sweat production for cooling the body: typically, 25° C. to 30° C. for a naked man at rest or 13° C. to 22° C. when clothed.

Efforts have been made to address these issues by bringing wearable sensors into nearly immediate contact with sweat as it emerges from the skin. A very recent example is the wearable patch presented by Gao et al. in "Fully integrated wearable sensor arrays for multiplexed in situ perspiration analysis" Nature 529, 509-514 (2016). The patch includes a sensor array for measuring $Na^+$, $K^+$, glucose, lactate, and skin temperature. However, the focus of this study is on the development and the integration of the sensors themselves which, whilst evidently crucial, does not address issues relating to sweat sample collection. The latter is mostly done by placing a several $cm^2$ sized absorbent pad between the skin and the sensor. The assumption is that, providing ample sweat is produced (hence tests are always done on individuals that heavily exercise), the pad will absorb the sweat for analysis, and newly generated sweat will refill the pad and 'rinse away' the old sweat. It is, however, likely that the time-dependent response of the sensor does not directly reflect the actual level of biomarkers over time because of accumulation effects. The sample collection and presentation to the published sensors may not be well-controlled so that continuous reliable sensing over a long period of time is difficult. Such patches may also not be designed to handle the tiny amounts of sweat that are produced under normal conditions, i.e. in the order of nanoliters per minute per sweat gland.

Continuous monitoring of high-risk patients, such as those with serious chronic conditions, pre- or post-operative patients, and the elderly, using sweat biomarker monitoring devices can provide higher quality diagnostic information than regular biomarker spot checks as normally done by repeatedly drawing multiple blood samples. Such continuous monitoring may be in a hospital setting or elsewhere. Human sweat alone or as mixture with sebum lipids may be an easily accessible source for biomarker measurements in wearable on-skin devices. For instance, cholesterol is an important biomarker associated with elevated risk in development of cardiovascular diseases. Inflammatory markers or cytokines, such as interleukins (e.g. TNF-a, IL-6) play an important role in the immune response and detection or disease monitoring of joint damage in rheumatoid and psoriatic arthritis, and bowel disease.

However, improvements are required to existing devices for continuous or intermittent monitoring. In wearable or portable devices for sweat monitoring, the detection of biomarkers or analytes in the biofluid of interest tends to require the device to include an analyte sensor having a surface on which capture species are immobilized; the capture species binding the biomarker. Typically, the capture species are antibodies and the analyte is a corresponding antigen. Alternatively, the detection principle may rely on a chemical, e.g. enzymatic, reaction involving the analyte. In both cases, the analyte detection/measurement may be dependent on the temperature.

EP 3242112 A1 discloses a method and device for liquid measurements comprising a sensor whose surface is arranged to receive a quantity of liquid, an electrical heating element arranged to heat said surface to force evaporation of the liquid, and an arrangement for measuring a temperature of said surface. Said temperature may be measured by measuring the electrical resistance of said electrical heating element.

WO 2017/058806 A1 discloses a wearable patch for making a sweat biomarker measurement. Skin temperature measurements acquired by a resistive temperature sensor are used to correct the biomarker concentration measurements made using an electrochemical sensor. A disadvantage of the system disclosed in WO 2017/058806 A1 is that the inclusion of an additional resistive temperature sensor increases the complexity and cost of the system. Such an additional temperature sensor also demands continual consumption of electrical energy which may render it unsuitable for use in sweat patches intended to be worn over relatively prolonged periods, such as over 7 to 28 days.

Providing a simple and low-cost sweat sensing system which accounts for such temperature dependency whilst enabling relatively long-term monitoring, such as over 7 to 28 day periods, remains a challenge.

SUMMARY OF THE INVENTION

The invention is defined by the independent claims. The dependent claims define advantageous embodiments.

According to an aspect there is provided a system for correcting a temperature-dependent sweat analyte measurement, the system comprising: a sweat collector for collecting sweat from skin; an outlet from which the sweat can evaporate; a capillary for transporting the sweat from the sweat collector to the outlet; a flow sensor for measuring a flow rate of the sweat through the capillary; an analyte sensor for obtaining the sweat analyte measurement from the sweat; and a controller configured to: determine a temperature from the measured flow rate; and correct the sweat analyte measurement based on the determined temperature.

Analyte measurements tend to be sensitive to the temperature at which the measurement is performed. This is because the measurement principle may rely on temperature-dependent processes, such as the binding of the analyte to a suitable functionalized surface, or a chemical, e.g. enzymatic, reaction involving the analyte. The temperature may influence the binding or chemical reaction of the analyte, which in turn affects the signal produced by the analyte sensor.

Sweat monitoring systems may, for instance, make use of a patch worn on the skin, i.e. on the periphery of the body. The temperature to which the patch, and the analyte sensor integrated therein, is exposed may therefore vary, e.g. between 20° C. to 40° C. Thus, for such sweat analyte measurements, being able to correct for the temperature dependency of the measurement is desirable.

A potential solution is to employ a conventional temperature sensor, such as a resistive temperature sensor, as an additional component of the sweat monitoring system in order to monitor the temperature. The continual power consumption associated with the use of such additional conventional temperature sensors may, however, be incompatible with the requirement for the sweat monitoring system to operate over relatively prolonged periods, such as 7 to 28 days. For such systems, ensuring minimal power consumption is important to ensure reliable operation over the monitoring period.

The present system uses a flow sensor in order to determine the temperature. The sweat evaporates from an outlet of a capillary to which the sweat is continually supplied from a sweat collector which collects the sweat from the skin. The sweat is driven through the capillary by capillary action and the evaporation of the sweat from the outlet. The flow sensor enables measurement of the flow rate of the sweat through the capillary. Because the evaporation of the sweat depends on the temperature, the flow rate serves as a proxy for the temperature. A controller thus determines the temperature from the measured flow rate, e.g. from a pre-determined correlation between the flow rate and the temperature. The controller is further configured to correct the analyte measurement based on the determined temperature.

A flow sensor tends to be already included in sweat sensing systems for the purpose of correcting the analyte measurement for variations in sweat excretion rate. The requirement to include a further sensing component, such as a resistive temperature sensor, for the purpose of correcting the analyte measurement for variations in temperature, is correspondingly obviated. In other words, the number of components required for the system need not be increased in order to measure the temperature, such that the physical complexity and cost of the system may be kept to a minimum. The power consumption of the system may also be reduced relative to a system employing an additional resistive temperature sensor.

The sweat collector, the capillary, the outlet, the flow sensor, and the analyte sensor may be at least partially housed within a patch for applying to the skin. The patch may provide a convenient means of housing the components. Moreover, by housing the capillary, the outlet and the flow sensor within the same patch as the analyte sensor, the determined temperature may be close to the temperature at which the analyte measurement takes place. This may facilitate the temperature correction of the analyte measurement.

The patch may include a thermally conductive layer arranged to conduct heat between the skin and the capillary, the outlet, the flow sensor, and the analyte sensor. In some embodiments, the system may be configured such that the difference between the skin temperature and ambient temperature is negligible, e.g. <1° C. In this case, the system may be regarded as operating under "isothermal conditions". This operating mode may, for example, partly determine the derivation of the temperature-flow rate correlation. The thermally conductive layer may assist the system to operate under such isothermal conditions. The thermally conductive layer may, for example, be fabricated from a metal or a metal alloy.

Alternatively, the patch may include a thermally insulating layer arranged to thermally insulate the capillary, the outlet, the flow sensor, and the analyte sensor from the skin. The temperature determination may be based on the flow rate of sweat under non-isothermal conditions, i.e. where the skin temperature is different from the ambient temperature. Accordingly, the thermally insulating material may create a stable and consistent temperature difference between the skin and the ambient air of several degrees Celsius, e.g. 5° C., under controlled environmental conditions such as those expected for patients in a hospital with a climate control system. The thermally insulating layer may, for example, be fabricated from a polymeric foam.

The thickness of the patch in which the sweat collector, the capillary, the outlet, the flow sensor, and the analyte sensor are located may be less than 10 mm, preferably less than 5 mm. Limiting the thickness of the patch in this manner may facilitate efficient heat transfer between the skin and the patch, which may be advantageous when the system is operated isothermally.

The system may comprise a vapor-receiving chamber for receiving the evaporated sweat from the outlet, wherein the vapor-receiving chamber is arranged relative to the outlet such as to shelter the outlet from ambient air flows. In this manner, the vapor-receiving chamber may assist to reduce the influence of such ambient air flows on the evaporation of sweat from the outlet, so that the temperature, rather than the velocity of the ambient air flow around the sensor, is determinative for the flow rate through the capillary.

The vapor-receiving chamber may comprise: a vent for permitting the evaporated sweat to escape to the atmosphere; and a desiccant in the vapor-receiving chamber for maintaining a humidity level in the vapor-receiving chamber over a period of time. The vapor-receiving chamber is open to the atmosphere via the vent but the effect of any variation in ambient humidity, which may otherwise influence the rate of sweat evaporation from the outlet, may be suppressed by the desiccant. The desiccant may be alternatively termed a "humidity absorber", owing to its function of absorbing moisture from the air inside the vapor-receiving chamber.

The system may comprise a porous body, wherein the pores of the porous body define the outlet. The porous body may be, for example, in the form of a porous membrane. The porous body may assist to ensure that the flow of sweat, and thus the temperature determination, is primarily governed by the evaporation of sweat from the porous body.

The controller may be configured to determine the temperature from the measured flow rate using a pre-determined correlation between the temperature and the flow rate. For convenient use of the correlation, the temperature determination may, for instance, be implemented using a lookup table.

The controller may be further configured to: determine a sweat rate from the measured flow rate; and correct the sweat analyte measurement based on the determined sweat rate. By correcting the analyte measurement for both temperature and sweat rate, the output relating to the analyte which is ultimately provided by the system may be more reliable and more straightforwardly comparable with measurements made under different temperature and sweat rate conditions.

The system may comprise an output device for communicating the corrected sweat analyte measurement to a user. The output device may include, for instance, a user interface for displaying the corrected analyte measurement.

According to a further aspect there is provided a method for correcting a temperature-dependent sweat analyte measurement, the method comprising: collecting sweat and supplying the sweat through a capillary to an outlet, the sweat being drawn through the capillary by capillary action and evaporation of the sweat from the outlet; measuring a flow rate of the sweat being drawn through the capillary; determining a temperature from the measured flow rate; obtaining the sweat analyte measurement from the sweat; and correcting the sweat analyte measurement based on the determined temperature.

The method may be performed using, for example, the system as defined above.

The determining a temperature from the measured flow rate may comprise using a pre-determined correlation between the temperature and the flow rate. The pre-determined correlation may, for example, be in the form of a lookup table.

These and other aspects of the invention will be apparent from and elucidated with reference to the embodiments described hereinafter.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Provided is a system for correcting a sweat analyte measurement for temperature. The system comprises a sweat collector for collecting sweat from skin. The collected sweat is drawn from the sweat collector to an outlet via a capillary. The sweat is drawn through the capillary by capillary action and evaporation of the sweat from the outlet. The evaporation of the sweat from the outlet depends on the temperature. A flow sensor measures a flow rate of the sweat being drawn through the capillary. An analyte sensor obtains the sweat analyte measurement. The system further comprises a controller which is configured to determine a temperature from the measured flow rate. The sweat analyte measurement is then corrected using the determined temperature.

The term "arrangement" may be regarded as an alternative for the term "system".

Fluctuations in the temperature of sweat sampled by a sweat patch may occur due to the sweat patch being worn on the periphery of the body, i.e. on the skin, where it may be exposed to physiological skin temperatures ranging from 20° C. to 40° C. Variations in skin temperature arise during the course of normal daily activity due to several factors including anatomical location, feeding, sleep, physical exercise, physical fitness level, body composition, metabolic syndrome factors, outdoor exposure, seasonal weather changes, and circadian rhythm, among others.

Analyte measurements tend to be sensitive to the temperature at which the measurement is performed. This is because the measurement principle may rely on binding of the analyte to a suitable functionalized surface, or on a chemical, e.g. enzymatic, reaction involving the analyte. The temperature may influence the binding or chemical reaction of the analyte, which in turn affects the signal produced by the analyte sensor. Accordingly, it is desirable to correct the analyte measurement in order to account for temperature variation.

Correcting the analyte measurement according to the temperature may be realized with a conventional temperature sensor, such as a resistive temperature sensor. However, the continual power consumption associated with the additional use of such conventional temperature sensors may be incompatible with the requirement for the sweat monitoring system to operate over relatively prolonged periods, such as 7 to 28 days. For such systems, ensuring minimal power consumption is important to ensure reliable operation over the monitoring period.

The present system therefore uses a flow sensor in order to determine the temperature. The sweat evaporates from an outlet of a capillary to which the sweat is continually supplied from a sweat collector which collects the sweat from the skin. The sweat is driven through the capillary by capillary action and the evaporation of the sweat. Because the evaporation of the sweat depends on the temperature, the flow rate of the sweat serves as a proxy for the temperature. The controller included in the system determines the temperature from the measured flow rate, e.g. from a predetermined correlation between the flow rate and the temperature. The controller then corrects the analyte measurement based on the determined temperature.

The system may make use of the flow sensor for the further purpose of correcting the analyte measurement for variations in sweat excretion rate. Accordingly, the flow sensor may serve a dual purpose, and obviate the requirement for a further sensing component, such as a resistive temperature sensor, for the purpose of correcting the analyte measurement for variations in temperature. This may assist to simplify the physical design of the system and reduce its cost to manufacture, since fewer components are required. Moreover, the power consumption of the system may also be reduced relative to a system employing an additional resistive temperature sensor.

When respective sensors for measuring the flow rate and the temperature, e.g. a flow rate sensor and thermistor, are employed, both sensors require power (Pf for the flow rate sensor and Pt for the temperature sensor) in order to perform their respective functions. In the present case, a single flow sensor only requires power Pf (as opposed to Pf+Pt when an additional temperature sensor is used). Whilst the flow sensor may need to be active for a longer time period in order to also fulfil the temperature sensing function, and thus might therefore consume slightly more energy, this would still be less than the energy consumed in the conventional scenario in which both the flow rate sensor and thermistor are used.

Because there may be variation in sweat rates, it may be expected that at very low sweat rates (<~0.05 nl/min/gland) there is some influence on the temperature determination as determined using the flow sensor. However, based on recent experiments, the inventors have found that a sweat rate of between 0.02-0.20 nl/min/gland is readily obtainable from sedentary individuals under ambient conditions; this rate being dependent on the number of active glands, which can vary, for example, between 10 to 100 glands per $cm^2$ in the forearm and palm regions. It is reasonable to assume that there are between ca. 10-30 active glands per $cm^2$ when an individual is sedentary under ambient conditions. This would imply a sweat rate of ~0.06-0.20 nl/min/gland, which is thought not to present any significant problem in relation to the temperature determination via sweat flow rate measurement. Also if lower sweat rates are deemed to be more clinically applicable, the patch geometry and dimensions may, for example, be tailored to accommodate these low sweat rates to ensure reliable temperature determination. Another approach to reduce the sweat rate dependence may be, for example, to include a further small sweat reservoir from which the sweat is drawn via the capillary channel due to evaporation.

Figure 1:
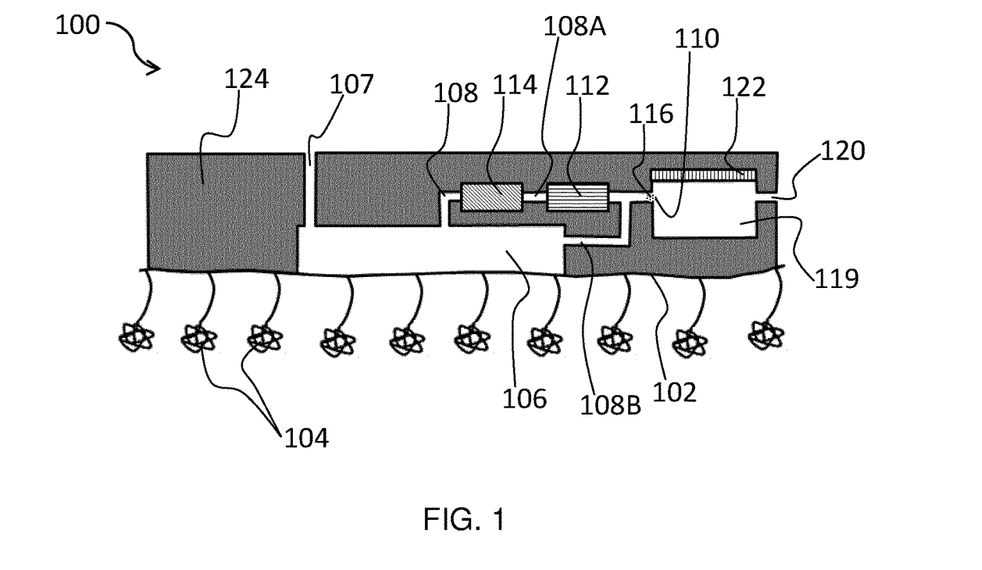
FIG. 1 schematically depicts a cross-section of a patch disposed on the skin according to an embodiment.

FIG. 1 schematically depicts a patch 100 which may be included in the sweat-sensing system. The patch 100 is shown adjacent an area of skin 102. The patch 100 may be applied to the skin 102 in any suitable manner for the purpose of sampling the sweat produced in the area of skin 102. For example, the patch 100 may be adhered to the skin 102 using a suitable biocompatible adhesive or secured to the skin by means of straps, as is well-known per se.

Sweat is excreted by sweat glands 104, and the sweat is collected by a sweat collector 106 which is included in the patch 100. As shown in FIG. 1, the sweat collector 106 may take the form of a recessed portion of the patch 100, having internal surfaces which, together with the skin 102, delimit a container in which the sweat may collect. An escape vent 107 may also be provided which permits evaporated sweat to escape from the sweat collector 106.

The sweat collector 106 is in fluid communication with a capillary 108. The capillary 108 extends to an outlet 110. The sweat is drawn from the sweat collector 106 through the capillary 108 by the combination of capillary action and evaporation of the sweat from the outlet 110.

After filling of the capillary 108, which may be alternatively termed a "microfluidic channel", the excess sweat may be removed due to evaporation of the sweat from the outlet 110, which facilitates flow in the capillary 108.

The flow rate of sweat through the capillary 108 is measured using the flow sensor 112. The flow sensor 112 may include any suitable flow sensor, such as an optical flow sensor and/or a thermal flow sensor, e.g. a calorimetric flow sensor or a temperature gradient driven flow sensor. Such flow sensors are well-known per se, and will not be further described herein for the sake of brevity only.

It is noted that the term "capillary" in the present context is not limited to a single tube or channel. In this respect, the capillary 108 shown in FIG. 1 comprises a plurality of paths 108A, 108B to the outlet 110. Path 108A passes via the flow sensor 112 and an analyte sensor 114, whereas path 108B does not pass via a sensor. The arrangement shown in FIG. 1 should not, however, be regarded as limiting, and any suitable arrangement of the capillary 108, analyte sensor 114 and flow sensor 112 may be contemplated. For example, the analyte sensor 114 may be arranged in a different fluid path from that of the capillary 108 and the flow sensor 112.

In an embodiment, a portion of the sweat collected by the sweat collector 106 is transported to the outlet 110 and the remainder is transported to the analyte sensor 114 for the analyte measurement, e.g. biomarker analysis.

The analyte sensor 114 may be regarded as the component which collects the analyte measurement data required for the analyte measurement. The analyte sensor 114 may rely on any detection principle suitable for sensing a sweat analyte. The analyte sensor 114 may, for example, comprise an electrochemical biosensor.

In a non-limiting example, the analyte sensor 114 comprises a sensor surface on which capture species are immobilized. The capture species may be selected to bind a particular analyte. For example, antibodies may be immobilized on the surface, which antibodies capture a particular antigen which is the analyte of interest. Thus, when a sample contacts the surface, the capture species may bind the analyte present in the sample. When the analyte is bound to the surface via the capture species, various detectable properties, e.g. optical and mechanical characteristics, of the surface are altered with respect to the analyte-free surface.

Alternatively or additionally, the analyte sensor 114 may comprise a sensor surface at which a reaction involving the analyte, e.g. an enzymatic reaction, may take place. The reaction may be detected, for instance, by electrochemical means. Such analyte sensing methods are well-known to the skilled person, and will not be further described herein for the sake of brevity only.

A porous body 116, such as a porous membrane, may be disposed at an end of the capillary 108. The pores of the porous body 116 may define the outlet 110. The porous body 116 may assist to ensure that a relatively strong capillary pull is provided, and that the flow of sweat, and thus the temperature determination, is primarily governed by the evaporation of sweat from the porous body 116.

The porous body 116 may be fabricated from any suitable material, such as a polymer, e.g. polyethylene terephthalate. A microporous structure may be provided in a polymer by, for example, using an excimer laser. The pores of the porous body 116 may, for example, have a diameter ranging from 50 μm to 250 μm.

By selection of the evaporation area provided by the porous body 116, the flow rate through the capillary 108 may be tuned, e.g. so as not to exceed an expected sweat rate. By avoiding the flow rate exceeding the expected flow rate, e.g. ca. 0.2 nl/min/gland, constant filling of the capillary 108 with sweat may be advantageously maintained.

In general, the rate of sweat evaporation depends on the ambient humidity, the ambient temperature, the skin temperature, and the velocity of ambient air flows. Physiologically speaking, human beings may lose excess metabolic heat by radiation, convection and sweat evaporation. Heat loss by convection and radiation may be very effective at low air temperatures, however, as the ambient temperature rises the effect of evaporative cooling by sweat becomes increasingly important for thermoregulation. Based on Dalton's law of partial pressures, sweat droplets excreted on the skin surface are in equilibrium between the liquid and gaseous phases, depending on the ambient temperature and humidity. The more sweat that is in the gaseous phase, the greater the heat loss, i.e. cooling effect, due to the latent heat of vaporization required for the phase change from liquid to gas.

As shown in FIG. 1, the patch 100 includes a vapor-receiving chamber 119 for receiving the evaporated sweat from the outlet 110. The vapor-receiving chamber 119 surrounds the outlet 110, and shelters the outlet 110 from ambient air flows. In this manner, the vapor-receiving chamber 119 may assist to reduce the influence of such ambient air flows on the evaporation of sweat from the outlet 110, so that the temperature, rather than the velocity of the ambient air flow around the sensor, is determinative for the flow rate through the capillary 108.

Whilst enclosing the outlet 110 within the patch 100 for the purpose of reducing the effect of ambient air flows may be preferable, compensating for variation in ambient air flows may be achieved in other ways. For example, other forms of shielding, such as positioning the patch 100 underneath clothing, may be contemplated.

Humidity may also be an important factor in determining the rate of sweat evaporation, since if the amount of water vapor already present in the air adjacent to the sweat drop is such that the gas portion is already filled, i.e. relative humidity (RH)=100%, then no evaporation will occur, and no cooling will take place. The highest sweat evaporation may occur at higher skin temperatures and lower relative humidity levels. However, under conditions of constant relative humidity the sweat evaporation rate will only depend on the ambient (≈skin/sweat) temperature enabling a direct linear correlation between the sweat evaporation rate and the skin temperature.

In the embodiment shown in FIG. 1, the vapor-receiving chamber 119 contains a desiccant 122. The moisture capacity and amount of the desiccant 122 may be selected such that the humidity in the vapor-receiving chamber 119 is maintained at a pre-determined level. By selecting a suitable amount and type of desiccant 122, the system may be permitted to operate within a larger dynamic range of sweat rate. The desiccant 122 may comprise, for instance, one or more of silica gel, calcium oxide and calcium sulphate. The vapor-receiving chamber 119 is open to the atmosphere via a vent 120 but the effect of any variation in ambient humidity, which may otherwise influence the rate of sweat evaporation from the outlet 110, may be suppressed by the desiccant 122.

Thus, the constant relative humidity provided in the vapor-receiving chamber 119 due to the desiccant 122 may make for a straightforward and reliable correlation between sweat flow rate and the temperature. The desiccant 122 may, however, be excluded, for example in scenarios where the ambient humidity is well-controlled, such as in a hospital setting, and/or where the system includes further sensory means for compensating for humidity variation.

The following is provided by way of non-limiting example in order to illustrate the utility of the desiccant 122 for maintaining the humidity level.

The amount of desiccant 122 required to control the humidity in the enclosed sweat patch 100 may depend on several variables, as may be seen from Equation 1.

$$Q = \frac{C_{eq}DVNt}{M_H F} \qquad \text{Equation 1}$$

where Q=quantity of desiccant (kg), $C_{eq}$=concentration of water vapor at equilibrium (g/m$^3$), D=decimal difference between the relative humidity (RH) outside the enclosure and the targeted RH inside (no unit), V=net volume of air in the enclosure (m$^3$), N=air exchange rate (1/day), t=minimum number of days the targeted RH range must be maintained (days), $M_H$=specific moisture reservoir of sorbent, including the effect of hysteresis (g/kg for a 1% RH change), F=targeted range of RH fluctuation (%).

The equilibrium concentration of water vapor (absolute humidity at saturation; 100% RH) may vary depending on the temperature (T in ° C.), e.g. 17.3 g/m$^3$ at 20° C.; 18.3 g/m$^3$ at 21° C.; 20.0 g/m$^3$ at 22.5° C. Concentrations at other temperatures may be obtained with Equation 2.

$$C_{eq} = 7.36 e^{(T/19.96)} - 2.75 \qquad \text{Equation 2}$$

Substituting Equation 2 into Equation 1 leads to:

$$Q = \frac{DVNt}{M_H F}\left(7.36 e^{\left(\frac{T}{19.96}\right)} - 2.75\right) \qquad \text{Equation 3}$$

Assuming the following: $C_{eq}$=20.0 g/m$^3$ of water vapor at equilibrium at 22.5° C.; ambient RH=80%; targeted RH in the housing=50%; D=0.30 (i.e. the difference between the ambient RH and the targeted RH); vapor-receiving chamber dimensions of 5 mm×5 mm×1 mm; V=2.5×10$^{-8}$ m$^3$ (net volume of air enclosed in the housing); N=1 air exchange rate (1/day); t=7 days (minimum number of days the targeted RH range must be maintained); $M_H$=3 g/kg for a 1% RH change; F=10% for the targeted range of RH fluctuation of ±5%, $$Q = \frac{(20.0)(0.30)(2.5*10^{-8})(1)(7)}{(3)(10)} = 3.5*10^{-8} \text{ kg} = 0.035 \text{ mg}$$

The small quantity of desiccant 122 required (0.035 mg) confirms the feasibility of the proposed approach for controlling the humidity of the air enclosed in the patch 100.

To illustrate how the temperature can be determined from the evaporation rate, the following exemplary scenario is presented in which the RH in the patch 100 is constant at 50% and the difference between skin and ambient temperature is negligible (<1° C., i.e. isothermal conditions). In this example, the air velocity over the patch 100 is assumed to be very low (≈0.001 m/s) and both the skin and ambient temperature are 35° C. It is possible to determine the evaporative sweat rate, $E_{SR}$, using the following Equation 4 (proposed by Nielsen B. Olympics in Atlanta: a fight against physics. Medicine & Science in Sports & Exercise. 1996; 28(6):665-8).

$$E_{SR} = 124\sqrt{v}(P_{sk} - P_a) * \frac{A}{E_{sw}} [Lh^{-1}] \quad \text{Equation 4}$$

where A=the total skin surface area, $E_{sw}$=rate of heat loss of sweat (≈675 WL$^{-1}$h), $P_{sk}$=average skin water vapor pressure, $P_a$=ambient water vapor pressure and v=air velocity.

Further, $P_{sk}$ and $P_a$ can both be determined from the water vapor saturation pressure of air (i.e. 100% humidity) which can be approximated using the following Equation 5.

$$P_{ws} = e^{(77.3450+0.0057T-7235/T)}/T^{8.2} \text{ [kPa]} \quad \text{Equation 5}$$

where T=the temperature in [K], which in the current example is $T_{sk}=T_a=35°$ C.+273.15 K=308.15 K. It is important to note here that the water vapor pressure of sweat, $P_{sk}$, as it is excreted from a sweat gland is at 100% humidity, while the water vapor pressure of the ambient, $P_a$, is at 30% humidity (due to the presence of the desiccant 122 in the enclosed patch 100).

Figure 2:
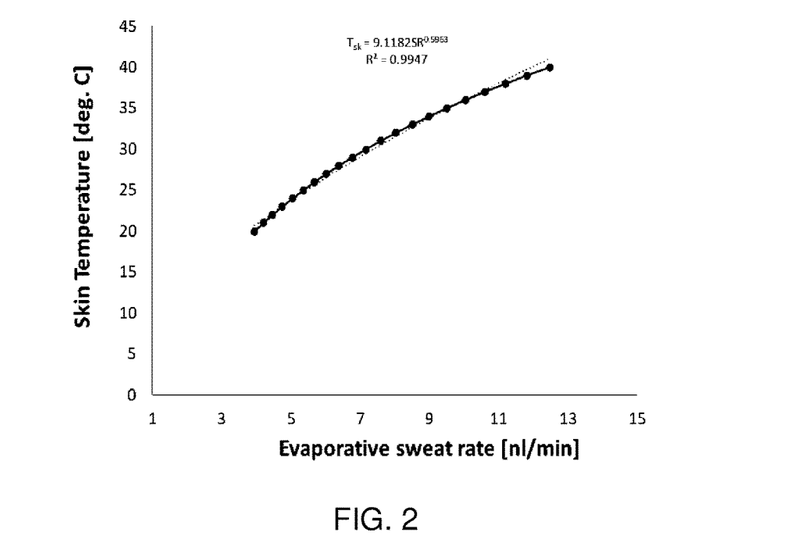
FIG. 2 provides a graph of skin temperature vs. evaporative sweat rate assuming that the skin temperature is the same as the ambient temperature.

Therefore, this implies:

$$P_{sk} = e^{(77.3450+0.0057*308.15-7235/308.15)}/(308.15)^{8.2} = 5.607 \text{ kPa}$$

$$P_a = 0.3 * e^{\left(77.3450+0.0057*308.15-\frac{7235}{308.15}\right)}/(308.15)^{8.2} = 1.682 \text{ kPa}$$

and, assuming that the skin area covered by the vapor-receiving chamber is 5 mm×5 mm, using Equation 4:

$E_{SR}$=124 $\sqrt{0.001}$(5.607−1.682)*2.5×10$^{-5}$/675=5.70×10$^{-7}$[$Lh^{-1}$]=9.50 nl/min The preceding analysis may be repeated over the range of physiological skin temperatures, i.e. 20° C. to 40° C., to obtain the correlation between the sweat evaporation rate and skin temperature, as shown in FIG. 2. The plot shown in FIG. 2 is based on the abovementioned assumed conditions (RH=30%, isothermal ($T_{sk}=T_a$), v=0.001 m/s, for a 5 mm×5 mm skin area covered by the patch 100).

Small deviations (<0.5° C.) from the isothermal boundary condition (i.e. $T_{sk} \approx T_a$) may lead to small, but acceptable, errors in the temperature estimation on the order of ≤0.5° C., in the 20° C. to 40° C. temperature range.

The body 124 of the patch 100 may be fabricated from any suitable material, such as a polymer, e.g. an elastomer. The material may, for example, be selected according to its thermal conductivity and depending on whether the skin temperature and the temperature of the vapor-receiving chamber 119 are intended to be the same (isothermal) or different (non-isothermal).

Similar considerations may apply to the thickness of the patch 100. In order to facilitate isothermal operation, the thickness of the patch 100 may be less than 10 mm. Preferably, the thickness is less than 5 mm in order for efficient heat transfer from the skin 102 to the patch 100.

Figure 3:
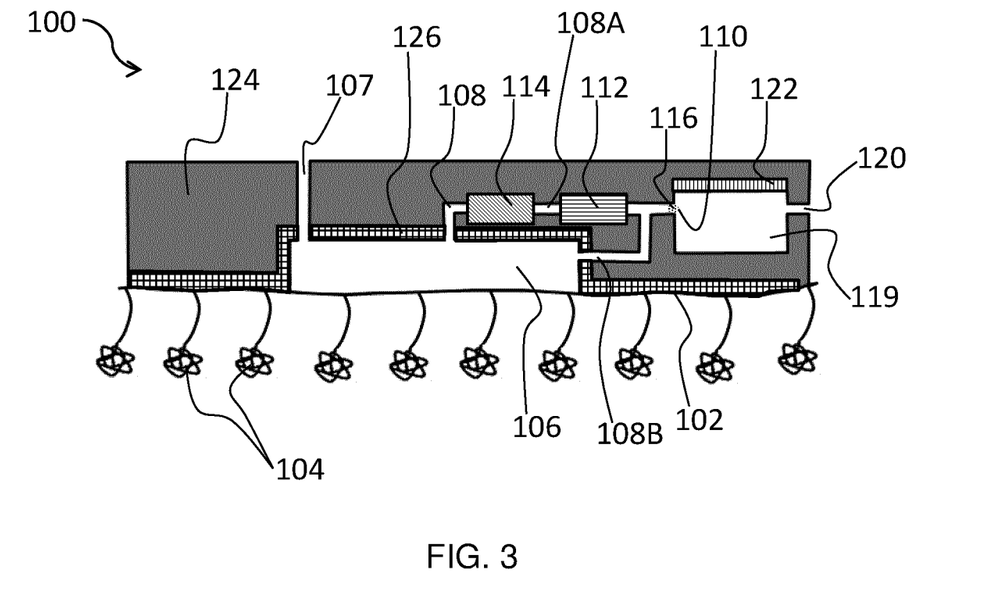
FIG. 3 schematically depicts a cross-section of a patch disposed on the skin according to another embodiment.

As schematically depicted in FIG. 3, when the system is intended to operate under the isothermal conditions described above, the patch 100 may include a thermally conductive layer 126 for conducting heat between the skin 102 and the capillary 108, the outlet 110, the flow sensor 112, and the analyte sensor 114. The thermally conductive layer 126 may, for example, be fabricated from a metal or a metal alloy.

In an alternative embodiment, the temperature determination is based on the evaporative flow rate of rate sweat under non-isothermal conditions, i.e. where the skin temperature is different from the ambient temperature ($T_{sk} \neq T_a$).

Whilst not shown in the Figures, this may be accomplished by using a patch 100 made from a relatively thick, e.g. 2-3 cm in thickness, thermally insulating material, such as a polymeric foam. The thermally insulating material may create a stable and consistent temperature difference between the skin 102 and the ambient air of several degrees Celsius (e.g. 5° C.) under controlled environmental conditions such as those expected for patients in a hospital with a climate control system.

The following is provided as an illustration of operation of the system under non-isothermal conditions. In this example, the room temperature is maintained at 25° C., while the skin temperature is at 35° C. By using Equation 5, and assuming 30% humidity for $P_a$, we obtain:

$$P_{sk,35} = e^{(77.3450+0.0057*308.15-7235/308.15)}/(308.15)^{8.2} = 5.607 \text{ kPa}$$

$$P_{a,25} = 0.3 * e^{\left(77.3450+0.0057*298.15-\frac{7235}{298.15}\right)}/(298.15)^{8.2} = 0.9476 \text{ kPa}$$

Figure 4:
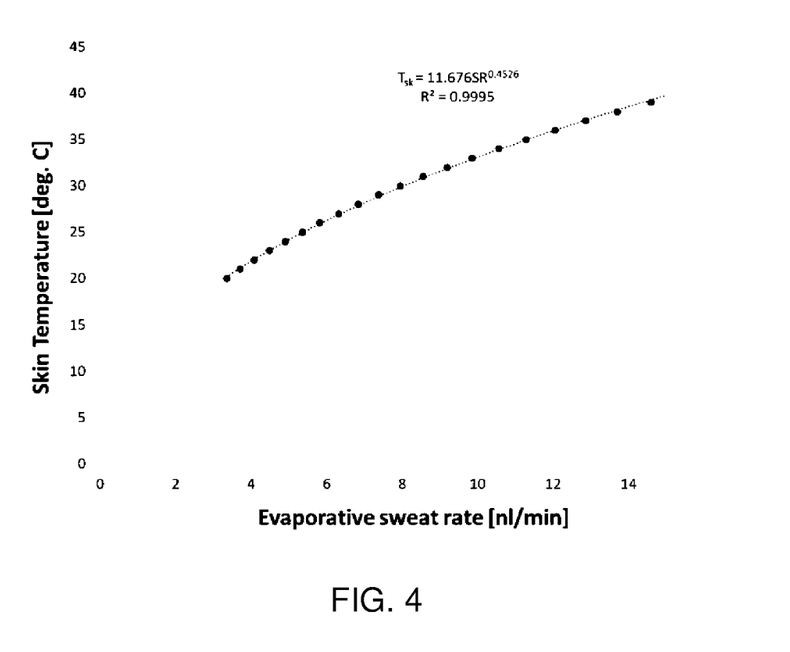
FIG. 4 provides a graph of skin temperature vs. evaporative sweat rate assuming that the skin temperature is different from the ambient temperature.

Assuming that the skin area covered by the vapor-receiving chamber is 5 mm×5 mm, using Equation 4:

$E_{SR}$=124 $\sqrt{0.001}$(5.607−0.9476)*2.5×10$^{-5}$/675=6.77×10$^{-7}$[$Lh^{-1}$]=11.28 nl/min The preceding analysis may be repeated over the range of physiological skin temperatures, i.e. 20° C. to 40° C., to obtain the non-isothermal correlation between the sweat evaporation rate and skin temperature, as shown in FIG. 4. The plot shown in FIG. 4 is based on the abovementioned assumed conditions (RH=30%, non-isothermal ($T_{sk} \neq T_a$), v=0.001 m/s, for a 5 mm×5 mm skin area covered by the patch 100, at a fixed ambient temperature of 25° C.).

A correlation between the flow rate and the sweat temperature can thus be readily established and used, for example, to create a lookup table. Once the sweat temperature is determined by measuring the evaporative flow rate, this can then be used to correct the analyte measurement, e.g. the measured biomarker concentration in sweat.

Figure 5:
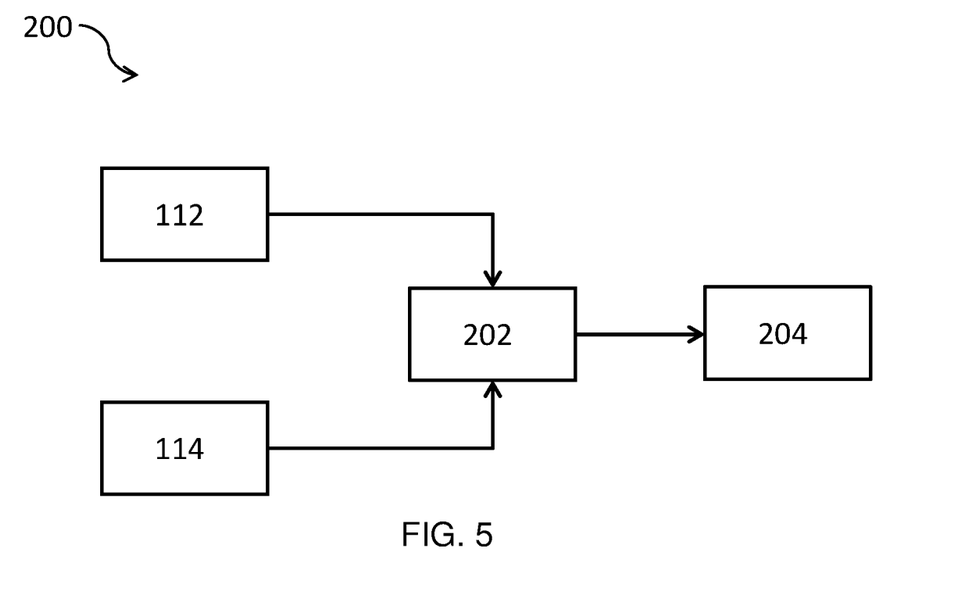
FIG. 5 provides a block diagram of a system according to an embodiment.

FIG. 5 shows a block diagram of a system 200 for correcting a temperature-dependent sweat analyte measurement. The arrow between the block representing the flow sensor 112 and the controller 202 denotes data relating to the flow of sweat in the capillary 108 being received by the controller 202. Similarly, the arrow between the block representing the analyte sensor 114 and the controller 202 denotes data relating to the analyte measurement being received by the controller 202.

The controller 202 uses the data relating to the flow of sweat in the capillary 108 to determine the temperature. This process may utilize a correlation between the flow rate and the temperature, as previously described. A lookup table may, for example, be used by the controller 202 in this process, although other means for determining the temperature from a relationship with the flow rate will be immediately apparent to the skilled person.

The controller 202 then uses the determined temperature to correct the analyte measurement. The analyte measurement may, for example, be corrected to what the measurement is predicted to be at a particular temperature, e.g. using a known relationship between the temperature and the analyte measurement. In this way, corrected analyte measurements may be compared to each other in spite of the respective temperatures at which the measurements actually took place being different from each other.

The corrected analyte measurement may then be passed from the controller 202 to an output device 204, which output device 204 communicates the corrected analyte measurement to a user, such as a patient and/or healthcare provider. The output device 204 may, for example, comprise a user interface for displaying the corrected analyte measurement. Alternatively or additionally, the output device 204 may comprise a suitable transmitter for transmitting the corrected measurement to an external device, such as a smartphone.

Whilst not shown in the Figures, it is noted that the controller 202 and/or the output device 204 may be included in the patch 100. Alternatively, some of the data processing implemented by the controller 202 may occur in a suitable module in the patch 100, and the remainder may be implemented on a separate data processing device. In this case, the patch 100 may include a suitable transmitter for transmitting the partially processed data to the separate data processing device. It may be advantageous to share the data processing with such a separate device in order to reduce the power consumption of the patch 100.

Figure 6:
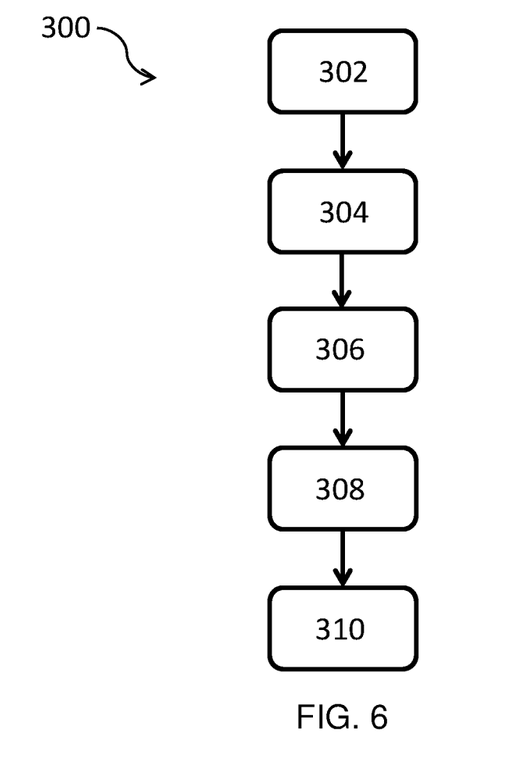
FIG. 6 provides a flowchart of a method according to an embodiment.

FIG. 6 provides a flowchart of a method 300 according to an embodiment. The method 300 may, for example, be implemented using the system 200 described above. The method 300 comprises, in a first step 302, collecting sweat and supplying the sweat through a capillary to an outlet. The sweat is drawn through the capillary by capillary action and evaporation of the sweat from the outlet, as previously described.

In step 304, a flow rate of the sweat drawn through the capillary is measured. The measured flow rate is then used to determine a temperature in step 306. Step 306 may, for instance, comprise using a pre-determined correlation between the temperature and the flow rate, as previously described.

In step 308, a sweat analyte measurement is obtained from the sweat. The sweat analyte measurement is then corrected in step 310 based on the determined temperature. This correction for temperature may ensure that a meaningful (corrected) analyte measurement is provided, which can be compared to other measurements, irrespective of the temperature conditions under which the measurements were taken.

Figure 7:
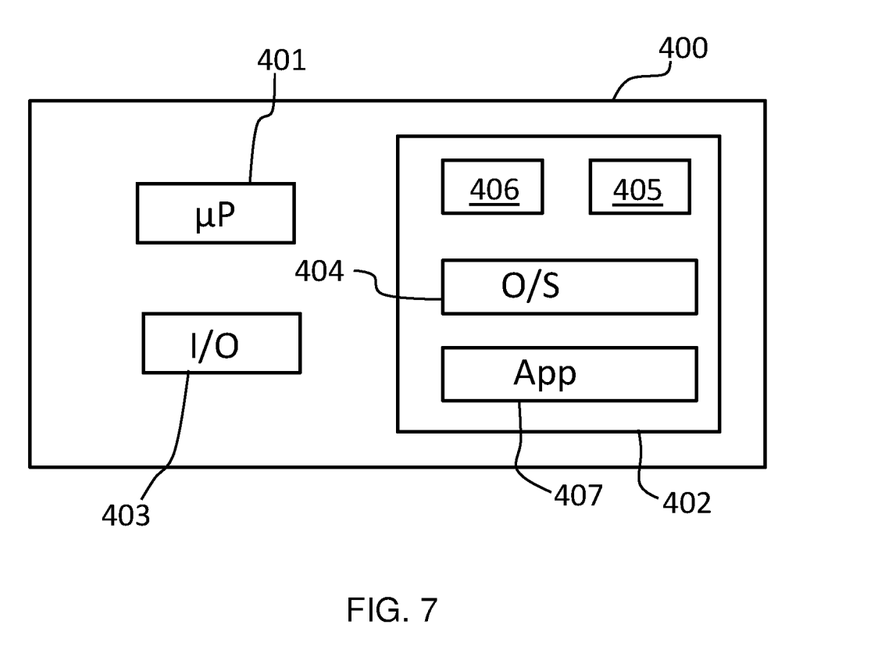
FIG. 7 shows a general computer architecture suitable for implementing the controller used in the system.

FIG. 7 illustrates an example of a computer 400 for implementing the controller 202 described above. The computer 400 includes, but is not limited to, PCs, workstations, laptops, PDAs, palm devices, servers, storages, and the like. Generally, in terms of hardware architecture, the computer 400 may include one or more processors 401, memory 402, and one or more I/O devices 403 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 401 is a hardware device for executing software that can be stored in the memory 402. The processor 401 can be virtually any custom made or commercially available processor, a central processing unit (CPU), a digital signal processor (DSP), or an auxiliary processor among several processors associated with the computer 400, and the processor 401 may be a semiconductor based microprocessor (in the form of a microchip) or a microprocessor.

The memory 402 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 402 may incorporate electronic, magnetic, optical, and/or other types of storage media. Note that the memory 402 can have a distributed architecture, where various components are situated remote from one another, but can be accessed by the processor 401.

The software in the memory 402 may include one or more separate programs, each of which comprises an ordered listing of executable instructions for implementing logical functions. The software in the memory 402 includes a suitable operating system (O/S) 404, compiler 405, source code 406, and one or more applications 407 in accordance with exemplary embodiments.

The application 407 comprises numerous functional components such as computational units, logic, functional units, processes, operations, virtual entities, and/or modules.

The operating system 404 controls the execution of computer programs, and provides scheduling, input-output control, file and data management, memory management, and communication control and related services.

Application 407 may be a source program, executable program (object code), script, or any other entity comprising a set of instructions to be performed. When a source program, then the program is usually translated via a compiler (such as the compiler 405), assembler, interpreter, or the like, which may or may not be included within the memory 402, so as to operate properly in connection with the operating system 404. Furthermore, the application 407 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 403 may include input devices such as, for example but not limited to, a mouse, keyboard, scanner, microphone, camera, etc. Furthermore, the I/O devices 403 may also include output devices, for example but not limited to a printer, display, etc. Finally, the I/O devices 403 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 403 also include components for communicating over various networks, such as the Internet or intranet.

When the computer 400 is in operation, the processor 401 is configured to execute software stored within the memory 402, to communicate data to and from the memory 402, and to generally control operations of the computer 400 pursuant to the software. The application 407 and the operating system 404 are read, in whole or in part, by the processor 401, perhaps buffered within the processor 401, and then executed.

When the application 407 is implemented in software it should be noted that the application 407 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

Non-invasive, semi-continuous and prolonged monitoring of biomarkers in sweat that indicate health and well-being is in demand for example for monitoring dehydration, stress, sleep, children's health and in perioperative monitoring, but can also be used for spot-check measurements. For example, the present disclosure may be applied in the field of patient monitoring as an early warning for sudden deterioration of patients in the General Ward, and for investigation of sleep disorders. This may represent an improvement since, currently, only measurements are only done in a spot-check fashion when a patient is visiting a doctor.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Measures recited in mutually different dependent claims may advantageously be used in combination. Any reference signs in the claims should not be construed as limiting the scope.

The invention claimed is:

1. A system for correcting a temperature-dependent sweat analyte measurement, the system comprising:
   a sweat collector configured to collect sweat from skin;
   an outlet from which the sweat can evaporate;
   a capillary configured to transport the sweat from the sweat collector to the outlet;
   a flow sensor configured to measure a flow rate of the sweat through the capillary;
   an analyte sensor configured to obtain the sweat analyte measurement from the sweat;
   a vapor-receiving chamber configured to receive the evaporated sweat from the outlet, wherein the vapor-receiving chamber is arranged relative to the outlet such as to shelter the outlet from ambient air flows; and
   a controller configured to:
      determine a temperature from the measured flow rate; and
      correct the sweat analyte measurement based on the determined temperature.

2. The system according to claim 1, wherein the sweat collector, the capillary, the outlet, the flow sensor, and the analyte sensor are at least partially housed within a patch configured to apply to the skin.

3. The system according to claim 2, wherein the patch includes a thermally conductive layer arranged to conduct heat between the skin and the capillary, the outlet, the flow sensor, and the analyte sensor.

4. The system according to claim 2, wherein the patch includes a thermally insulating layer arranged to thermally insulate the capillary, the outlet, the flow sensor, and the analyte sensor from the skin.

5. The system according to claim 2, wherein a thickness of the patch in which the sweat collector, the capillary, the outlet, the flow sensor, and the analyte sensor are located is less than 10 mm, preferably less than 5 mm.

6. The system according to claim 1, wherein the vapor-receiving chamber comprises:
   a vent configured to permit the evaporated sweat to escape to the atmosphere; and
   a desiccant in the vapor-receiving chamber configured to maintain a humidity level in the vapor-receiving chamber over a period of time.

7. The system according to claim 1, comprising a porous body, wherein the pores of the porous body define the outlet.

8. The system according to claim 7, wherein the porous body is in the form of a porous membrane.

9. The system according to claim 1, wherein the controller is configured to determine the temperature from the measured flow rate using a pre-determined correlation between the temperature and the flow rate.

10. The system according to claim 9, wherein the pre-determined correlation is in the form of a lookup table.

11. The system according to claim 1, wherein the controller is further configured to:
    determine a sweat rate from the measured flow rate; and
    correct the sweat analyte measurement based on the determined sweat rate.

12. The system according to claim 1, comprising an output device configured to communicate the corrected sweat analyte measurement to a user.

13. A method for correcting a temperature-dependent sweat analyte measurement, the method comprising:
    collecting sweat and supplying the sweat through a capillary to an outlet, the sweat being drawn through the capillary by capillary action and evaporation of the sweat from the outlet;
    measuring flow rate of the sweat through the capillary;
    determining a temperature from the measured flow rate;
    receiving the evaporated sweat from the outlet in a vapor-receiving chamber, wherein the vapor-receiving chamber is arranged relative to the outlet such as to shelter the outlet from ambient air flows;
    obtaining the sweat analyte measurement from the sweat; and
    correcting the sweat analyte measurement based on the determined temperature.

14. The method according to claim 13, wherein the determining a temperature from the measured flow rate comprises using a pre-determined correlation between the temperature and the flow rate.

15. The method according to claim 13, further comprising:
    determining a sweat rate from the measured flow rate; and
    correcting the sweat analyte measurement based on the determined sweat rate.

16. The method according to claim 13, further comprising a patch configured to apply to skin, wherein a sweat collector, the capillary, the outlet, a flow sensor, and an analyte sensor are at least partially housed within a patch configured to apply to the skin.

17. The method according to claim 16, wherein the patch includes a thermally conductive layer arranged to conduct heat between the skin and the capillary, the outlet, the flow sensor, and the analyte sensor.

18. The method according to claim 16, wherein the patch includes a thermally insulating layer arranged to thermally insulate the capillary, the outlet, the flow sensor, and the analyte sensor from the skin.

19. The method according to claim 16, wherein a thickness of the patch in which the sweat collector, the capillary, the outlet, the flow sensor, and the analyte sensor are located is less than 10 mm, preferably less than 5 mm.

* * * * *